United States Patent
Callahan et al.

(10) Patent No.: US 6,517,577 B1
(45) Date of Patent: Feb. 11, 2003

(54) CROSSED HAPTICS FOR INTRAOCULAR LENSES

(75) Inventors: Wayne B. Callahan, Abington, VA (US); J. Scott Callahan, Blountville, TN (US)

(73) Assignee: ThinOptX, Inc., Abingdon, VA (US)

( * ) Notice: Subject to any disclaimer, the term of this patent is extended or adjusted under 35 U.S.C. 154(b) by 0 days.

(21) Appl. No.: 09/568,019

(22) Filed: May 10, 2000

Related U.S. Application Data

(63) Continuation-in-part of application No. 09/084,989, filed on May 28, 1998, now Pat. No. 6,083,261.

(51) Int. Cl.[7] .................................................. A61F 2/16
(52) U.S. Cl. ...................... 623/6.49; 623/6.52; 623/6.46
(58) Field of Search ......................... 623/6.11, 6.38, 623/6.39, 6.4, 6.41–6.43, 645–6.49, 6.51, 6.52

(56) References Cited

U.S. PATENT DOCUMENTS

| | | | |
|---|---|---|---|
| 4,254,509 A | | 3/1981 | Tennant |
| 4,573,998 A | | 3/1986 | Mazzocco |
| 4,581,033 A | * | 4/1986 | Callahan ........................ 623/6 |
| 4,585,456 A | | 4/1986 | Blackmore |
| 4,591,358 A | * | 5/1986 | Kelman ........................ 623/6 |
| 4,655,775 A | | 4/1987 | Clasby, III |
| 4,687,484 A | * | 8/1987 | Kaplan ........................ 623/6 |
| 4,711,638 A | | 12/1987 | Lindstrom |
| 4,764,169 A | * | 8/1988 | Grendahl ........................ 623/6 |
| 4,769,035 A | | 9/1988 | Kelman |
| 4,795,460 A | | 1/1989 | Anis |
| 4,804,361 A | | 2/1989 | Anis |
| 4,816,032 A | | 3/1989 | Hetland |
| 4,842,600 A | | 6/1989 | Feaster |
| 4,863,463 A | | 9/1989 | Tjan |
| 4,878,911 A | | 11/1989 | Anis |
| 4,950,290 A | | 8/1990 | Kammerling |
| 4,994,080 A | | 2/1991 | Shepard |

(List continued on next page.)

FOREIGN PATENT DOCUMENTS

| | | |
|---|---|---|
| DE | 3722910 | 1/1989 |
| DE | 4030005 | 3/1992 |
| FR | 2653325 | 4/1991 |
| FR | 2666503 | 3/1992 |
| FR | 2687304 | 8/1993 |
| GB | 2124500 | 2/1984 |
| SU | 1377086 | 11/1986 |

*Primary Examiner*—David J. Isabella
*Assistant Examiner*—Urmi Chattopadhyay
(74) *Attorney, Agent, or Firm*—Waddey & Patterson, PC; Douglas W. Schelling

(57) ABSTRACT

A crossed haptics attached to an intraocular lens suitable for implantation in either a phakic or an aphakic eye and a method for implanting and releasing the haptics after implantation in the eye, wherein. The lens comprises a very thin, deformable optic having two pairs of haptics attached to the optic by means of two stems 180° apart on the circumference of the optic, the stems being wider and thinner at the base attached to the periphery of the optic, and tapering to a narrower and thicker tip to which each haptic is connected at opposite edges of the stem. Each haptic optionally sweeps about the periphery of the optic so that the angle subtended by a radial line extending from the center of the optic through the center of a footplate and a second radial line extending from the center of the optic through the center of the stem to which it attaches is about 135°. Also disclosed is a haptic design comprising four footplates which are all independently attached to an optic transition area. The optic transition area is the area where the haptics engage the optic. This embodiment is preferably inserted into the eye by a rolling method. As such, this embodiment provides a lens with excellent flexibility and allows the haptics to be placed inside a rolled optic and return to their natural shape when unrolled.

15 Claims, 6 Drawing Sheets

U.S. PATENT DOCUMENTS

| | | |
|---|---|---|
| 5,098,444 A | 3/1992 | Feaster |
| 5,108,429 A | 4/1992 | Wiley |
| 5,118,452 A | 6/1992 | Lindsey et al. |
| 5,171,320 A | 12/1992 | Nishi |
| 5,197,981 A * | 3/1993 | Southard .................. 623/6 |
| 5,258,025 A | 11/1993 | Fedorov et al. |
| 5,266,074 A | 11/1993 | Nishi et al. |
| 5,366,501 A | 11/1994 | Langerman |
| 5,443,506 A | 8/1995 | Garabet |
| 5,480,428 A | 1/1996 | Fedorov et al. |
| 5,489,302 A | 2/1996 | Skottun |
| 5,522,890 A | 6/1996 | Nakajima et al. |

* cited by examiner

OPTICAL DISPLACEMENT IS THE
DIFFERENCE IN THE SAGITTA OF A
LENS AT REST AND A LENS COMPRESSED

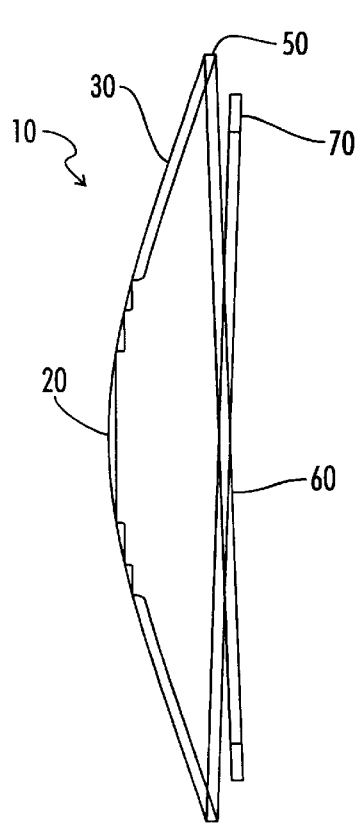 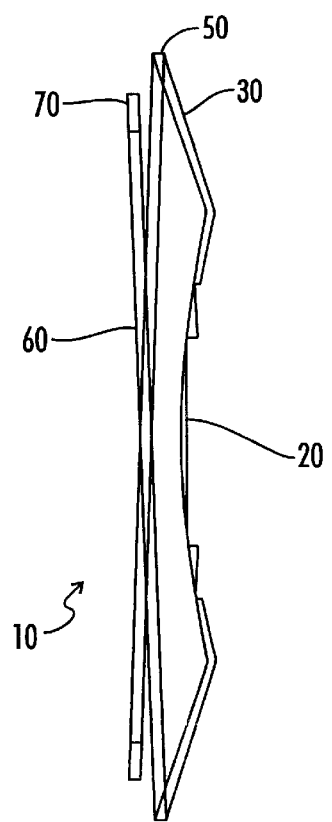 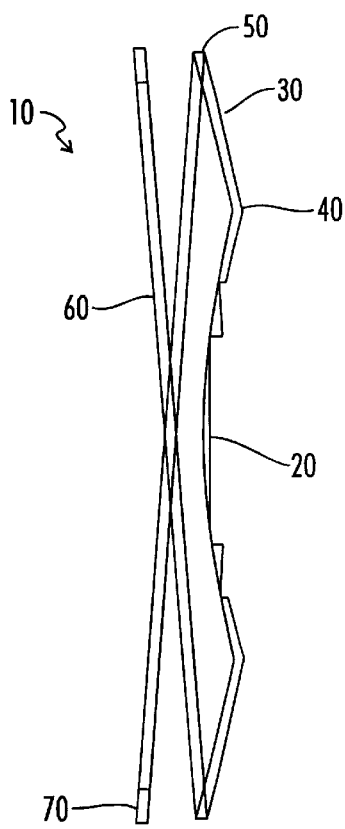
FIG. 11   FIG. 12   FIG. 13
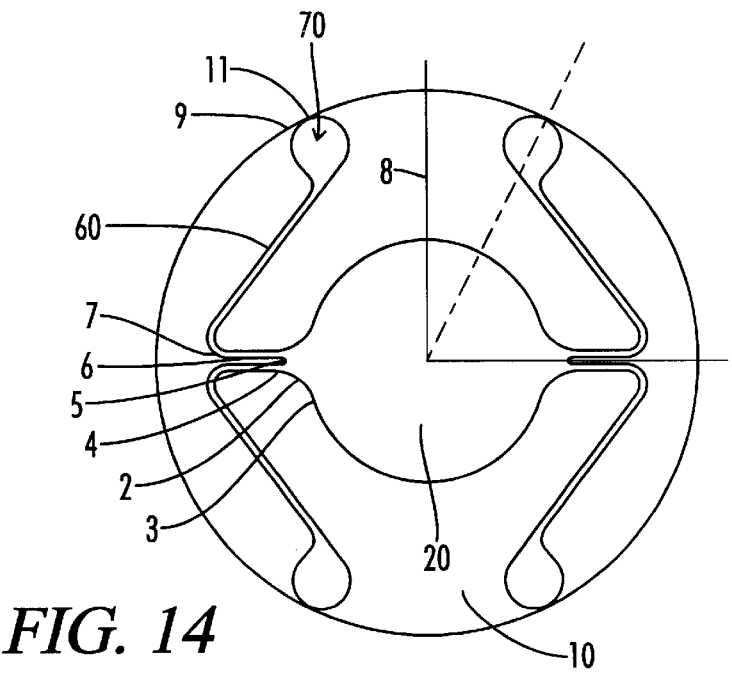
FIG. 14

CROSSED HAPTICS FOR INTRAOCULAR LENSES

The present application is a Continuation-in-part application of U.S. Ser. No. 09/084,989, filed May 28, 1998, now U.S. Pat. No. 6,083,261 for "Crossed Haptics for Intraocular Lenses"; the contents of which are expressly incorporated herein by reference.

BACKGROUND OF THE INVENTION

1. Field of the Invention

The present invention relates the field of ophthalmology, and particularly to crossed haptics for intraocular lenses ("IOL"), the intraocular lenses comprising the haptics are suitable for implantation of an appropriate optic in either a phakic or an aphakic eye. One suitable optic is a thin lens where the optic is rolled into a circle or oval and the haptics are placed inside the optic when rolled.

2. Anatomy of the Eye

The human eye functions much like a camera. It accommodates to changing lighting conditions and focuses light rays originating from various distances from the eye. When all of the components of the eye function properly, light is converted to impulses and conveyed to the brain where an image is perceived. See Northwest Kansas Eye Clinic website Dec. 6, 1999, "How The Eye Works," Glaucoma, Ocular Anatomy and Function.

Light rays enter the eye through a transparent layer of tissue known as the cornea. The surface that a contact lens rests upon is the outer surface of the cornea. The outer surface is also known as the epithelium layer of the cornea. The inner surface of the cornea is the endothelium. As the eye's main focusing element, the cornea takes widely diverging rays of light and bends them through the pupil, the dark, round opening in the center of the colored iris. With the condition Myopia or nearsightedness, if the eye is too long, or the cornea has too much focusing power, images focus in front of the retina. The light rays have passed the correct focal point by the time they reach the retina. The retina then sends an "over-focused," blurry image to the brain. Hyperopia, or farsightedness, is the opposite of myopia; images focus on a point beyond the retina. This condition is a result of an eye that is too short or a cornea that lacks the necessary refractive power to focus images on the retina. Note the main focusing element of light rays entering the eye is the cornea. Light rays then pass through the anterior chamber of the eye, which is the area between the inside of the cornea and the iris.

The lens of the eye is located immediately behind the iris and pupil. The purpose of the lens is to make the delicate adjustments in the path of the light rays in order to bring the light rays into focus upon the retina, the membrane containing photoreceptor nerve cells that lines the inside back wall of the eye. The photoreceptor nerve cells of the retina change the light rays into electrical impulse and send them through the optic nerve to the brain where an image is perceived.

For the purpose of the present disclosure, common definitions known to one of ordinary skill in the art are used for common parts of the eye. For example, the cornea is understood as being the transparent, outer "window" and primary focusing element of the eye. The outer layer of the cornea is known as epithelium. Its main job is to protect the eye. The epithelium is made up of transparent cells that have the ability to regenerate quickly. The inner layer of the cornea, endothelium, is also made up of transparent tissue, which allows light to pass; however, the endothelium does not regenerate when damaged.

The pupil is the dark opening in the center of the colored iris that controls how much light enters the eye. The colored iris functions like the iris of a camera, opening and closing, to control the amount of light entering through the pupil.

The lens is the part of the eye immediately behind the iris that performs delicate focusing of light rays upon the retina. In persons under 40, the lens is soft and pliable, allowing for fine focusing from a wide variety of distances. For individuals over 40, the lens begins to become less pliable, making focusing upon objects near to the eye more difficult. This is known as presbyopia.

The retina is the membrane lining the back of the eye that contains photoreceptor cells. These photoreceptor nerve cells react to the presence and intensity of light by sending an impulse to the brain via the optic nerve. In the brain, the multitude of nerve impulses received from the photoreceptor cells in the retina is assimilated into an image.

Finally, the anterior chamber is the small space between the cornea, endothelium, and the iris. The pupil is the central hole in the iris. The natural lens of the eye is located immediately behind the iris. The anterior chamber is filled with a clear fluid that carries oxygen and nutrients to the cornea and lens. Metabolic waste products produced by the lens and cornea are also removed by this fluid. An organ called the ciliary body located behind the iris constantly produces fresh fluid called aqueous. The fluid then circulates from behind the iris through the pupil, moves through the anterior chamber and finally exits through a drainage mechanism called Schlemm's Canal. See FIG. 1, a photograph of a slide, with the arrow pointing to Schlemm's Canal.

The entrance to the canal is a filtering network called the trabecular meshwork. The fluid produced by the ciliary body meets some resistance when exiting the anterior chamber through the trabecular meshwork causing pressure to build up inside the eye. The balance between the amount of aqueous production and the ease of drainage through the trabecular meshwork is very important. If the aqueous is produced at higher rate than the rate of drainage, the pressure inside the eye will rise. If it rises high enough, damage to the optic nerve will occur with associated loss of visual function. The condition of unbalanced pressure in the eye is called glaucoma. Uncorrected glaucoma can lead to permanent blindness.

2. Description of the Prior Art

Ophthalmologists have been developing the art of implanting an artificial lens in the human eye for many years, both to replace the natural lens which has been removed due to disease (an aphakic eye), and to supplement the natural lens with a corrective lens (a phakic eye).

Various pathologic disease processes can cause deterioration of the natural lens requiring removal of the lens, most notably the opacification of the lens which occurs in cataracts. In the developmental stage, cataracts may be treated by frequent changes of eyeglass prescription. When useful vision is lost, the natural lens is generally removed, either intact or by emulsification. When the lens has been removed, correction is achieved either through spectacles, contact lenses, or an intraocular implant.

Over fifty years ago, an ophthalmologist implanted the first lens after the removal of the natural lens due to cataracts (aphakic eye). The early lenses were placed in the anterior chamber of the human eye. From the initial implants, surgeons wanted a lens where radically one size would fit all eyes. The initial lenses were constructed from one piece of material where the optic and haptic footplates were part of a solid piece of material. A typical lens from the late 1970's is shown in FIG. 2.

By the early 1980's, technology was developed to where the haptic foot plates and the optic could be connected from one piece of material using stems approximately 200 microns in diameter. For anterior chamber aphakic implants the lens are still very popular in 1999; however, over 97 percent of all cataract operations are done by placing a lens in the posterior chamber of the eye. Most surgeons begin using posterior chamber lens because anterior chamber lens required radial sizing to fit the eye and blocked the aqueous flow through a portion of the trabecular meshwork. If the sizing was not perfect, additional pressure was placed on the trabecular meshwork, which projected additional pressure on Schlemm's Canal, this further restricted aqueous flow. Blocking aqueous flow increases the internal pressure of the eye (i.e., glaucoma). An additional problem with the anterior chamber lens is the footplates are approximately 250 microns thick, which restricts the portion of the trabecular meshwork where the footplate is contacting the tissue. After most of the profession changed to posterior chamber lens, a small incision posterior chamber lens was developed. The state of the art anterior chamber lens still requires an incision larger than the optic diameter of the lens. After twenty years of use, the Kelman lens is still a popular anterior chamber lens for cataract surgery. A typical Kelman lens is shown in FIG. 3.

From the drawings, it is apparent that the Kelman lens is much more flexible than the earlier models. However, the manufacturer still markets six different radial lengths of the lens ranging from 11.5 to 14.5 millimeters. Recently, samples for the lens were obtained and the force required to flex the lens one millimeter ranged from 1.5 to 4.0 grams. The manufacturer supplies a chart, which does not show inserting the lens in an eye where the flexure is greater than one millimeter.

Optical displacement is the amount of movement of the lens along the optical axis of the lens when compressed using the at rest measurement as reference (see FIG. 4). Another way of stating optical displacement is when the lens fits into a large eye there is very little pressure applied to the haptics to position the lens. When the same lens is placed into a smaller eye more pressure is required to fit the lens into the eye. When the additional pressure is necessary the lens will move forward toward the endothelium.

The difference in position between the small eye and large eye anterior placement is the optical displacement. Recent measurements of the Kelman style lens versus the current invention show comparable optical displacemrent. Both style lenses have optical displacement of less than 25 micron.

When compressed, the dimension referred to as Sagitta in an uncompressed lens increases. The difference in the Sagitta of a lens at rest and the same dimension of a compressed lens is optical displacement.

Due to the problems and the availability of a very good posterior chamber lens, much of the aphakic eye surgery previously done with anterior chamber lens changed to the posterior chamber lens. The largest advantage of the posterior chamber lens was the development of posterior chamber lens that will pass through a small incision. By 1990 over 80 percent of cataract surgery was being done with small incision posterior chamber lens.

In the 1980's, surgeons began doing Radial Keratotomy (RK) to correct myopia. Later surgeons learned Photorefractive Keratectomy (PRK) was a more effective treatment of myopia and in the 1990's LASIK (laser in situ keratomileusis) surgery became popular. LASIK is effective over a much larger power range. In RK, and PRK the cornea is cut to relax the tissue, which reduces the amount of bending of light as it passes into the eye. LASIK surgery removes a layer of tissue from the middle layer of the cornea, which has the effect of flattening the cornea, to reduce the bending of light as it enters the eye. PRK and LASIK surgery is done using a laser. Of course, most vision correction is accomplished using contact lens and spectacles. As an alternative to the laser surgeries, contact lens, and spectacles, ophthalmologists are implanting lens in the eye with the natural lens still in place (phakic eye). The lens can also be used in conjunction with another method of treatment. For example, for a high myopic patient the ophthalmologist may make part of the correction using PRK or LASIK surgery, and then implanting the lens for the remainder of the needed correction. The lens can also be used to correct for hyperopia (farsightedness) using a positive powered lens. The depth of the anterior chamber of the human eye is deeper for a myopic eye than for a hyperopic eye; therefore, the clearance to place the lens and haptic in the anterior chamber is less. The depth of the anterior chamber of the eye varies and so does the width of the eye. One would normally expect a deep eye to be narrower than a shallow eye; therefore, the haptics on all lenses being placed in the anterior chamber of the human eye must be sized to fit the eye.

Making different lengths of haptics and having the surgeon measure the anterior diameter of the eye can accomplish the sizing. A second method is to have the haptic portion of the lens maintain a near constant force when compressed to fit a smaller eye.

For almost twenty years, small incision posterior chamber lens have been available. A small incision lens for the anterior chamber is needed. For the phakic eye, the physical dimensions of the lens in the axial plane must be small. Nothing is being removed from the eye, so the amount of space to place the lens optic and haptics are limited.

Traditionally vision problems such as myopia, hypermetropia and astigmatism have been treated with corrective lenses in spectacles or contact lenses. However, as significant improvements and experience has been gained, the use of intraocular implants using corrective lenses has increased.

Generally, the lens separates the aqueous humor from the vitreous body. The iris separates the region between the cornea or anterior of the eye and the lens into an anterior chamber and a posterior chamber. The lens itself is contained in a membrane known as the capsule or capsular sac. When the lens is removed from the eye, the capsule may also be removed (intracapsular excision), or the anterior portion of the capsule may be removed with the lens leaving the posterior portion of the capsule intact (extracapsular extraction), often leaving small folds or flaps from the anterior portion of the capsule. In an intraocular implant, the artificial or prosthetic lens may be inserted in the anterior chamber, the posterior chamber, or the capsular sac. The artificial lenses are usually fixedly attached within the eye, either by stitching to the iris, or by some supporting means or arms attached to the lens, often in the form of sweeping arms called haptics.

Examples of lens for implantation in the anterior chamber include: U.S. Pat. No. 4,254,509, issued Mar. 10, 1981 to Jerald L. Tennant (an accommodating lens with 2 haptics 180° apart arched posteriorly to optic, with an arc at the end of each haptic defining feet); U.S. Pat. No. 4,816,032, issued Mar. 28, 1989 to Jens G. Hetland (optic with a hole in the center to equalize pressure and prevent glaucoma, having 2 loop haptics); and Soviet Invention Certification No. SU 1377086, published Nov. 4, 1986 (optic with two pairs of crossed haptics).

An example of a lens for implantation in the posterior chamber is shown in U.S. Pat. No. 5,108,429, issued Apr. 28, 1992 (optic with concentric support ring attached by micrometers controlled by computer to adjust the position of the lens for loss of focal power or astigmatism resulting from the surgery).

A number of advances have dealt with implants in the capsular bag, which attempt to take advantage of the capsular membrane to avoid damage to the tissue of the eye. Among them are: U.S. Pat. No. 4,711,638, issued Dec. 8, 1987 to Richard L. Lindstrom (2 haptics attached to one quadrant of optic, forming semicircles on opposite sides of the optic, and open ended 180° from their point of attachment); U.S. Pat. No. 4,795,460, issued Jan. 3, 1989 to Aziz Y. Anis (2 haptics circumferentially surrounding optic by about 350°, attached to the optic 180° apart); U.S. Pat. No. 4,804,361, issued Feb. 14, 1989, also to Anis (optic surrounded by supporting ring connected to optic by two elongated, curved members); U.S. Pat. No. 4,842,6900, issued Jun. 27, 1989 to Fred T. Feaster (a single haptic overlapping itself with a noose at the end for guiding the haptic); U.S. Pat. No. 4,863,463, issued Sep. 5, 1989 to Tik T. Tjan (optic with concentric supporting ring attached by two elongated, curved members); U.S. Pat. No. 4,878,911, issued Nov. 7, 1989 to Aziz Y. Anis (optic with concentric supporting ring connected by 2 straight segments 180° apart); U.S. Pat. No. 5,171,320, issued Dec. 15, 1992 to Okihiro Nishi (optic with grooves on periphery receiving anterior flaps of capsule); U.S. Pat. No. 5,266,074, issued Nov. 30, 1993 to Nishi, et al. (same as above, but with different shapes for periphery); U.S. Pat. No. 5,366,501, issued Nov. 22, 1994 to David W. Langerman (optic with two concentric support rings attached by straight bars, the outer ring angled anteriorly); U.S. Pat. No. 4,655,775, issued Apr. 7, 1987 to Thomas J. Clasby III (optic with ridges to offset optic from posterior surface of posterior chamber, having 2 bent haptics); and U.S. Pat. No. 4,950,290, issued Aug. 21, 1990 to William Kammerling (lens to reduce posterior capsular opacification, having biconvex optic with helically shaped loop haptic sloping 10° anterior to the optic).

Examples of correcting lenses are described in U.S. Pat. No. 4,585,456, issued Apr. 29, 1986 to John M. Blackmore (corrective lens in contact with natural lens, having 2 appendages or haptics fitting into the ciliary sulcus); U.S. Pat. No. 4,769,035, issued Sep. 6, 1988 to Charles D. Kelman (corrective lens with folding optic and two broad haptics 180° apart, each having an arc at the free end to define feet, the optic being folded and inserted in the posterior chamber through the pupil); U.S. Pat. No. 5,098,444, issued Mar. 24, 1992 to Fred T. Feaster (optic glued to anterior surface of natural lens); U.S. Pat. No. 5,258,025, issued Nov. 2, 1993 to Fedorov, et al. (optic with same radius of curvature as natural lens, two broad haptics having feet fitting in Zinn's zonules); U.S. Pat. No. 5,480,428, issued Jan. 2, 1996, also to Fedorov, et al. (corrective lens floating in the eye); and our own pending application (a deformable intraocular corrective lens with 2 curved haptic 180° apart).

Examples of accommodating lenses are shown in U.S. Pat. No. 5,443,506, issued Aug. 22, 1995 to Antoine L. Garabet (varying the power of the lens by a fluid loop through a first optic, the fluids having differing refractive indices and responding to electrical impulses from the ciliary body); U.S. Pat. No. 5,489,302, issued Feb. 6, 1996 to Bernt C. Skottun (lens with fluid and membranes responding to change in pressure caused by ciliary muscle, changing volume of fluid and refractive index of lens).

U.S. Pat. No. 4,573,998, issued Mar. 4, 1986 to Thomas P. Mazzocco, describes various arrangements of haptics, none of which are crossed, and various methods for implanting deformable intraocular lenses, none of which describe using a viscoelastic material to join seriated sutures. U.S. Pat. No. 4,994,080, issued Feb. 19, 1991 to Dennis P. Shepard, shows an optic with at least one opening to improve focusing for depth, with embodiments having either 2 or 4 haptics, none being crossed. U.S. Pat. No. 5,522,890, issued Jun. 4, 1996 to Nakajimi, et al., discloses a deformable lens having two haptics attached to the optic using right angled reinforcements at the periphery of the optic which are thicker than the periphery, the lens being folded into a tube shape for implantation in the eye.

Some foreign patents showing slightly different arrangements of the haptics include: U.K. Patent No. 2,124,500, published Feb. 22, 1984 (annular ring attached to optic by fibers); German Patent No. 3,722,910, published Jan. 19, 1989 (two haptics, each having a substantially quarter moon shape); French Patent No. 2,653,325, published Apr. 26, 1991 (an annular haptic bound to haptic by a bridge, and 180° away by a convex loop); French Patent No. 2,666,503, published Mar. 13, 1992 (two haptics joining optic on the same side, extending in semicircle on opposite side of optic, and having a stop to prevent crossing of haptics); German Patent No. 4,040,005, published Mar. 26, 1992 (two haptics spreading out from a common bridge to optic); and French Patent No. 2,687,304 published Aug. 20, 1993 (optic with annular support ring joined to optic by two bridges).

Despite the advances, there remain problems with intraocular implants which may be ameliorated by the improved haptics and method of releasing the haptics of the present invention inside the bulb of the eye. When an intraocular lens is inserted in the eye, an incision is made in the cornea or sclera. The incision causes the cornea to vary in thickness, leading to an uneven surface which causes astigmatism. The insertion of a rigid lens through the incision, event with compressible haptics, requires an incision large enough to accommodate the rigid lens (at least 6 mm), and carries with it the increased risk of complications, such as infection, laceration of the ocular tissues, and retinal detachment. Deformable intraocular lenses made from polymethylmethacrylate ("PMMA"), polysulfone, silicone or hydrogel may be inserted through a smaller incision, about 4 mm or less.

Nevertheless, it is critical that the lens be properly centered and properly fixed so that it does not slip out of position. In an anterior chamber implant, the lens should be positioned between the cornea and the iris, but avoiding contact with either to prevent corneal damage, proliferation of corneal epithelium on the anterior surface of the lens causing opacification, or iritis. If the lens is not positioned properly with respect to the pupil, too much light may be admitted to the retina, causing serious vision difficulties. The haptics or lens support generally lodge in the angle of the anterior chamber, but it is desirable that the haptics be as flexible as possible while keeping the area of surface contact between the haptic and the eye tissue as small as possible to avoid swelling, laceration, infection, or other damage to the eye tissue.

The anterior chamber of the eye is filled with the aqueous humor, a fluid secreted by the ciliary process, passing from the posterior chamber to the anterior chamber through the pupil, and from the angle of the anterior chamber it passes into the spaces of Fontana to the pectinate villi through which it is filtered into the venous canal of Schlemm. The lens must be positioned so the flow of fluid is not blocked or glaucoma may result. If the haptics fit slightly too tight, the patient experiences pain and the lens may have to be removed. If the haptics are slightly too loose, the lens may move into the endothelial cells on the inside of the cornea causing permanent loss of vision.

Posterior chamber and capsular bag implants involve both similar and different considerations. In posterior chamber implants, the haptics normally lodge in the ciliary sulcus, entailing the same considerations with regard to tissue swelling and damage through laceration. Most posterior chamber implants are placed in in the posterior capsule in order to take advantage of the insulating properties of the capsule membrane. Here, it is desirable to stretch the capsule as much as possible, vaulting the optic posteriorly to avoid having the anterior flaps proliferate and opacify the anterior surface of the lens, and to stretch the capsule taut. The corrective lens for the phakic eye must be extremely thin in order to fit into the limited space in either the anterior or posterior chambers with the natural lens still in place, but must have some area of thickness at the periphery of the lens to support attachment of the haptics.

Regardless of the type of implant, some means of centering the implant is essential. Currently artificial lenses are implanted using special tools to compress the haptics, such as forceps or cannulas, or rely on microhooks to manipulate the optic through a hole in the surface of the optic. Haptics designed to center in the eye and means for compressing the haptics without the use of bulky tools during centering is therefore desirable.

The present invention solves these problems by a deformable intraocular lens having two pairs of crossed haptics with footplates connected to the optic by a stem. The lens is inserted into the eye using a unique method of compressing the haptics by seriated sutures temporarily joined using a viscoelastic material, which is dissolved after centering the lens in the eye.

Although the Soviet Invention Certificate SU 1,377,086 also shows crossed haptics, it is noted that (1) the optic is rigid, requiring a longer incision (6 mm) and the increased risk of complications during insertion, as well as restricting use to anterior chamber implants; (2) the haptics do not have footplates, placing more surface area of the haptic in contact with the eye tissue; (3) there is not stem between adjacent haptics, but rather each haptic is individually attached to the haptic, requiring the periphery of the lens to be thick enough for attachment of the haptics; and (4) the haptics extend outwardly from the optic for ¾ of their length before turning concavely towards the lens, virtually precluding compressing the haptics either in front of or behind the lens, presenting a longer profile for insertion through the incision.

Thus, none of the above inventions and patents, taken either singularly or in combination, are seen to describe the instant invention as claimed. Hence the crossed haptics for intraocular lenses solving the aforementioned problems is desired.

3. Discussion of Haptic Deflection Formulas

All materials have some deflection when force is applied. For the purpose of haptic design, a material is chosen that has a flexibility that allows the lens to remain stationary in the plane parallel with the central axis of the lens, yet is flexible when constructed to the desired thickness in the radial plane. As stated above, the position of the optic is very important, with potentially serious adverse effects occurring when an optic is improperly positioned. For the most part, the lens haptics are constructed from plastic, which responds to deflection according to the following formula:

$$f \approx WL^3/EI$$

Where:
f=Deflection of the haptic
W=Amount of force applied to the end of the haptic
L=Length of the haptic
I=Moment of inertia of the haptic material.
$\approx$ is a sign to show numbers are proportional instead of equal. In the present case, constants have been omitted.

$$I \approx hw^3$$

h=vertical height of the haptic
w=width of the haptic
E=Modulus of elasticity of the haptic material.

The modulus of elasticity (E) is the ratio of the increment of unit stress to increment of unit deformation within the elastic limit of the material. See Standard Handbook for Mechanical Engineers, Theodore Baumeister, Editor, and Marks Editor, 1916 to 1951, McGraw Hill Book Company, New York Sixth Edition Pages 5–42.

According to Hooke's Law, when force is applied along an axis the increase in length due to application of the force divided by the original length of the member along the axis to which force is applied is strain. See Mechanics of Materials by E. P. Popov Professor of Civil Engineering University of California Prentice-Hall, Inc. Englewood Cliffs, N.J., Page 29.

Strain is a dimensionless quantity, and is very small except for materials such as rubber. Stress is the amount of force applied to a material divided by the cross Sectional area of the material where the stress was applied. When plotting a relationship between stress and strain, there is a portion of the diagram that is linear. The deflections where the stress strain diagram is linear do not cause a permanent deformation of the material to which the stress was applied. For some materials, such as cast iron and concrete the portion of the curve where there is no permanent deformation is extremely small. For some alloy steels the curve is linear almost to the rupture point of the material. Up to some point, the relationship between stress and strain may be said to be linear for all materials.

This is known as Hooke's Law. Stress is directly proportional to strain and the constant of proportionality is called the elastic modulus, modulus of elasticity, or Young's modulus. The elastic modulus has been bench tested and calculated for many materials and published in engineering and other scientific handbooks. The formula for deflection can be stated as the amount of deflection of a beam, the haptic, is proportional to the applied force times the length of the deflected object, haptic, to the third power divided by the modulus of elasticity times a coefficient and the moment of inertia of the material being deflected. The inertia of the material in a rectangular shape can be expressed as the width of the haptic times the height of the haptic to the third power divided by a constant. In addition, when a material of rectangular shape is deflected and the amount of deflection is held constant, over time the amount of stress in the material will reduce. For example, haptics of rectangular dimensions were made using the present invention. The haptics were deflected three millimeters and the applied force measured. After twenty-four hours, the amount of applied force to retain the three-millimeter deflection had decayed to less than 25 per cent of the original deflection force.

4. Discussion of Mechanical Properties

Shear stress is defined as stress arising in practice when applied forces are transmitted from one part of a body to the other by causing stresses in the plane parallel to the applied force. See FIG. 5.

Stress in a beam caused by bending can be represented by the equation:

$$Sb = Mc/I$$

Where
  Sb=the stress on the beam from bending.
  M=the bending moment which is the force times the bending arm.
  I=the moment of inertia for the cross Section
  c.=The distance for the stressed edge to the neutral axis of the beam.

In addition, when an object in compression rests against another object that is in equilibrium, the transferred pressure is equal to the applied force divided by the area in contact. Which can be written as:

$$P = F/A$$

Where:
  P=pressure applied to support the member that is compressed.
  F=force applied to hold compressed member in equilibrium.
  A=area between the compressed member and supporting member that is in contact.

5. Discussion of Haptic Deflection

Using the deflection formulas one can see the deflection is proportional to the applied force times the length of the beam (or haptic) to the third power. The modulus of elasticity for a given material is constant if one assumes the material to be homogenous.

As shown by FIG. 6, the moment of inertia for a rectangular structure is the width of the cross section of the material times the height of the cross section of the material to the third power.

Therefore one can write the formula for deflection as:

$$f \approx WL^3/EI$$

Where:
  $I \approx hw^3$
Therefore:

$$f \approx WL^3/E\,hw^3$$

Since E is a constant, the formula can be written:

$$f \approx WL^3/hw^3$$

The textbook formula is shown for deflection in the vertical plane. The current invention desires to eliminate as much movement axially, which is known as anterior displacement. Yet the current invention desires to make the haptics much more flexible than the current state of the art. The flexure equation must be written as two ways. The first equation represents deflection in the radial plane and can be written as:

$$f \approx WL^3/tw^3$$

Where:
  t=thickness of the haptic and is measured parallel to the central axis of the lens.
  w=the width of the haptic and is measured along the radial plane.
  W=applied force in the radial plane.
  L=length of the beam.

If "t" is decreased while "w" is held constant, the amount of deflection for a given force will increase. Conversely, as "t" decreases the amount of force required to deflect the beam is proportionally decreased. However, as "w" is decreased the amount of force to deflect the beam is decreased by the third power of the width. Therefore the radial deflection of the beam or haptic is much more influenced by the width of the beam or haptic than the thickness.

For deflection in the axial plane the equation can be written as:

$$f \approx WL^3/wt^3$$

Where:
  W=the applied force in the axial direction.
  L=the length of the beam or haptic.
  'w=the width of the beam or haptic measured in the radial plane.
  't=the thickness of the beam or haptic measured in the axial plane.

Deflection in the vertical plane is proportional to the third power of the thickness and proportional to the width of the haptic or beam. Since radial displacement is proportional to the third power of the width and proportional to the thickness, one can readily see by increasing the thickness of the beam and reducing the width of a beam, the beam will become much more flexible while resisting deflection in the axial plane. For the desired lens, increasing the thickness reduces the axial displacement and decreasing the width of the haptic, increases the radial flexure.

The haptics on the Kelman anterior chamber lens that is widely used have a haptic that is approximately 175 microns square. Whereas, certain embodiments of the current invention have haptics that are approximately 175 by 100 microns, the 100-micron dimension is found in the radial plane and is raised to third power. Therefore, the current invention has a cross sectional area that is designed to be much more flexible than the current state of the art lens. The Kelman Lens with the overall radial diameter of 14 millimeters has haptic members that are approximately 7¼ millimeters from the optic to the first footplate and an additional 4½ millimeters from the first footplate to the second footplate. Since the second footplate pivots from the first footplate, it is obvious the two-footplates do not exert the same amount of force for a given displacement. The haptic members on such embodiments are approximately 8 millimeters from the optic to the footplate on each haptic. The dimensions will cause the current invention's footplates to be slightly more flexible than the first footplate of the Kelman Lens. The second footplate of the Kelman Lens will be more flexible than the current invention, since the Kelman Lens second haptic pivots from the first haptic. Therefore, haptics diagonally across on the Kelman Lens will have approximately the same force while the alternate haptics have a different force. The force will attempt to reach equilibrium, so the lens may de-center to balance the forces. The current invention has all the forces equal so the lens centration is much more easily achieved.

SUMMARY OF THE INVENTION

The present invention comprises crossed haptics attached to an intraocular lens suitable for implantation in either a phakic or an aphakic eye and a method for implanting and releasing the haptics after implantation in the eye. The lens comprises a very thin, deformable optic having two pairs of haptics attached to the optic by means of two stems 180° apart on the circumference of the optic, the stems being wider and thinner at the base attached to the periphery of the optic, and tapering to a narrower and thicker tip to which each haptic is connected at opposite edges of the stem. Each haptic optionally sweeps about the periphery of the optic so that the angle subtended by a radial line extending from the center of the optic through the center of a footplate and a second radial line extending from the center of the optic through the center of the stem to which it attaches is about 135°. The lens is symmetrical about an axis extending through the opposing stems, with each haptic crossing either over or under the haptic connected to the opposing stem on the same side of the axis. This embodiment of the present invention may be inserted into the eye by using a previously prepared seriated suture joined by a viscoelastic material to fold the lens in a tubular shape and compress the haptics, inserting the lens in the eye, centering the lens, dissolving the viscoelastic material with saline solution, and removing the seriated suture by pulling a free end of the suture left outside the eye during insertion. When released, the footplates of the four haptics lie on the circumference of a circle concentric with the optic, subtending four substantially equal arcs.

Accordingly, it is a principal object of the invention to provide crossed haptics for intraocular lenses suitable for implantation into either a phakic or an aphakic eye which may be centered in the eye easily in the form of a deformable lens having crossed haptics with footplates at their free ends which may be inserted in the eye using seriated sutures temporarily joined by a viscoelastic material to compress the lens and haptics in a tubular shape, dissolving the viscoelastic material and removing the suture after centering the lens.

It is another object of the invention to provide crossed haptics for intraocular lenses suitable for implantation into either a phakic or an aphakic eye which may be centered in the eye easily in the form of a deformable lens having two pairs of crossed haptics with footplates wherein the position of the lens is fixed in the eye by four foot plates lying on the circumference of a circle concentric with the optic and subtending substantially equal arcs.

It is a further object of the invention to provide crossed haptics for intraocular lenses suitable for implantation into either a phakic or an aphakic eye in which damage to the tissue of the eye is reduced by minimizing haptic contact with the eye to four footplates sized and shaped to exert a minimum of pressure on the tissues of the eye.

Still another object of the invention is to provide crossed haptics for intraocular lenses suitable for implantation into either a phakic or an aphakic eye having two pairs of crossed haptics attached to the optic by a pair of stems in which the lens may be implanted in the anterior chamber, the posterior chamber, or the capsular sac, depending on the conformation of the lens.

It is an object of the invention to provide improved elements and arrangements, thereof for the purposes described which is inexpensive, dependable and fully effective in accomplishing its intended purposes.

It is another object of the invention to provide a haptic design comprising four footplates which are all independently attached to an optic transition area. The optic transition area is the area where the haptics engage the optic. This embodiment is preferably inserted into the eye by a rolling method. As such, this embodiment provides a lens with excellent flexibility and allows the haptics to be placed inside a rolled optic and return to their natural shape when unrolled.

These and other objects of the present invention will become readily apparent upon further review of the following specification and drawings.

BRIEF DESCRIPTION OF THE DRAWINGS

FIG. 11 is a plan view of the a first embodiment of an intraocular lens with crossed haptics according to the present invention adapted for insertion into the anterior chamber of an aphakic eye.

FIG. 12 is a plan view of a second embodiment of an intraocular lens with crossed haptics according to the present invention adapted for insertion into the posterior chamber of an aphakic eye.

FIG. 13 is a plan view of a third embodiment of an intraocular lens with crossed haptics according to the present invention adapted for insertion into the posterior chamber of a phakic eye.

FIG. 14 is an embodiment of an intraocular lens of the present invention featuring four haptics all independently attached to the optic transition area.

DETAILED DESCRIPTION OF THE PREFERRED EMBODIMENTS

The present invention relates to crossed haptics for intraocular lenses and a method for inserting the lens into the bulb of the eye and releasing the haptics. Haptics are spring-like structures which support the optic of an intraocular lens implant in order to maintain the lens in a relatively fixed position within the eye.

Figure 1:
FIG. 1 is a view of an anterior chamber of an eye and Schlemm's Canal.
Figure 2:
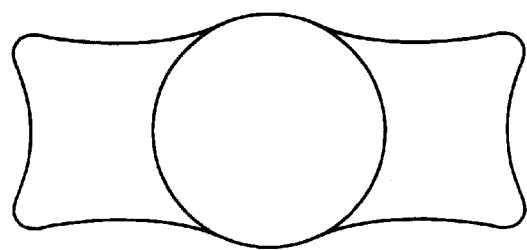
FIG. 2 is a view of a prior art, one-piece lens.
Figure 3:
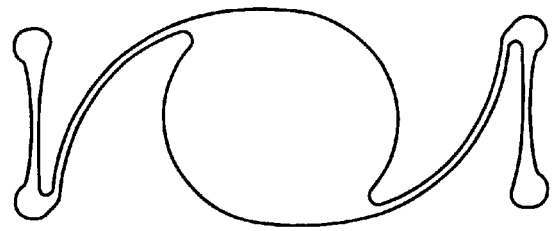
FIG. 3 is a view of a prior art Kelman lens.
Figure 4:
FIG. 4 is a graph showing optical displacement.
Figure 5:
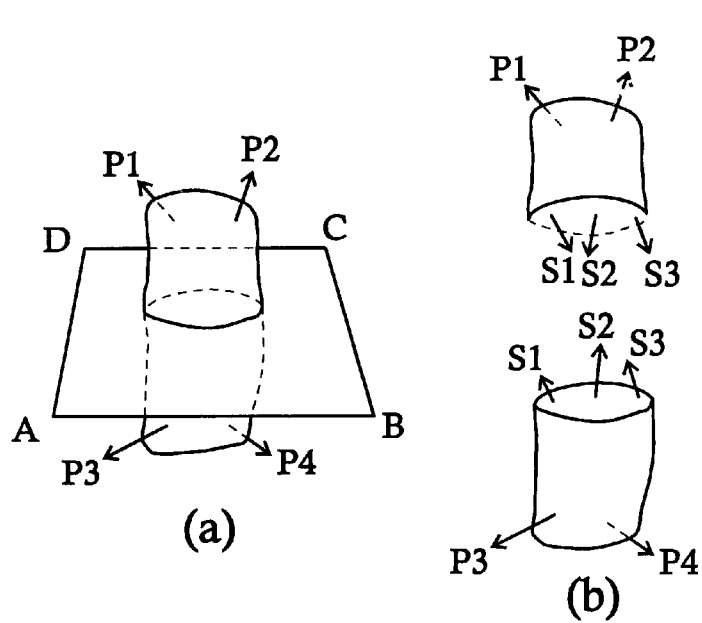
FIG. 5 is a figure showing a measurement of a value for sheer stress.
Figure 6:
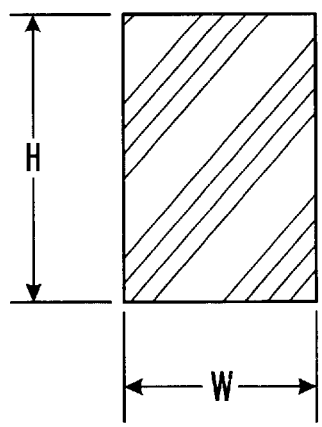
FIG. 6 is a figure demonstrating values of the moment of inertia.
Figure 7:
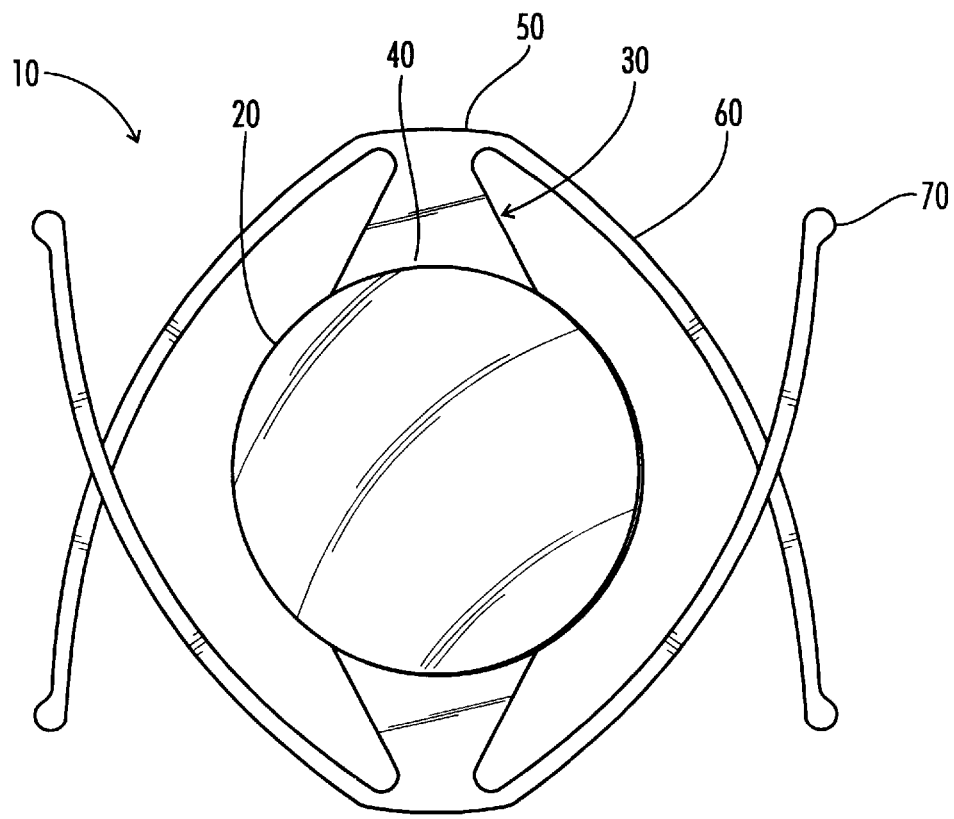
FIG. 7 is a front elevational view of crossed haptics for intraocular lenses according to the present invention.

FIG. 7 shows an intraocular lens, designated generally as reference 10 in the Figures, showing exemplary crossed haptics 60 according to the present invention. The lens comprises a central optical portion referred to as the optic 20. The optic 20 is designed to replace the natural lens in an aphakic eye, or to supplement and correct defects in the natural lens in a phakic eye. The optic 20 will generally be constructed in varying thicknesses, shapes (generally disk shaped, with its outer surfaces biconvex, plano-convex, etc.), and focal powers or properties according to the application. The crossed haptics 60 of the present invention are designed to be used with optics 20 having different optical properties. However, they are intended for use with and are integral with deformable optics 20 made from polymethylmethacrylate ("PMMA"), polysulfone, silicone or hydrogel, preferably PMMA, and are capable of being deformed by compressing, rolling folding, stretching, etc. for insertion into the eye through a small incision, but being somewhat resilient and having memory characteristics to revert to their original shape when the force procuding deformation is removed. In the preferred embodiment, the optic 20 is about 6 mm in diameter and the edge of the optic is about 0.050 mm thick.

A pair of substantially flat stems, designated generally as 30, extend from the edges of optic 20, each stem having a line of symmetry separated from the other by approximately 180°. The base 40 of the stem 30 is wide and thin where it attaches to the edge of the optic 20, being about 3 mm wide and 0.05 mm thick. As it extends radially from optic 20, the stem 30 becomes progressively narrower and thicker, being about 1 mm wide and 0.127 mm thick at the tip 50 or free end of the stem 30.

Each stem 30 has a pair of haptic arms 60 attached to opposite edges of the stem 30 near the tip 50. The width of the stem 30 at its base 40 and the thickness of the stem 30 at its tip 50 provide strength and a secure anchor for mounting the haptic 60 arms to the optic 20, while retaining a sufficiently flexible stem 30 to manipulate the haptics 60 as set forth below.

Each of the haptic arms 60 has a footplate 70 at its free end. The footplates 70 are small, rounded protrusions at the end of the haptics 60 extending slightly laterally from the outer edge of the haptic 60. The haptic arms 60 are arcuately shaped and extend from opposite sides of the tip 50 of the stem 30, being concave relative to the edge of the optic 20. Along a radial line extending from the center of the optic 20, the tip of the stem is about 4.75 mm from the center of the optic 20 and the outer edge of each footplate 70 rests in a circle about 7 mm from the center of the optic 20. Each haptic 60 sweeps about the periphery of the optic 20 so that the angle subtended by a radial line extending from the center of the optic 20 through the center of a footplate 70 and a second radial line extending from the center of the optic 20 through the center of the stem 30 to which it attaches is about 135°. The lens 10 is symmetrical about an axis extending through the opposing stems 30, with each haptic 60 crossing either over or under the haptic 60 connected to the opposing stem 30 on the same side of the axis.

Figure 8:
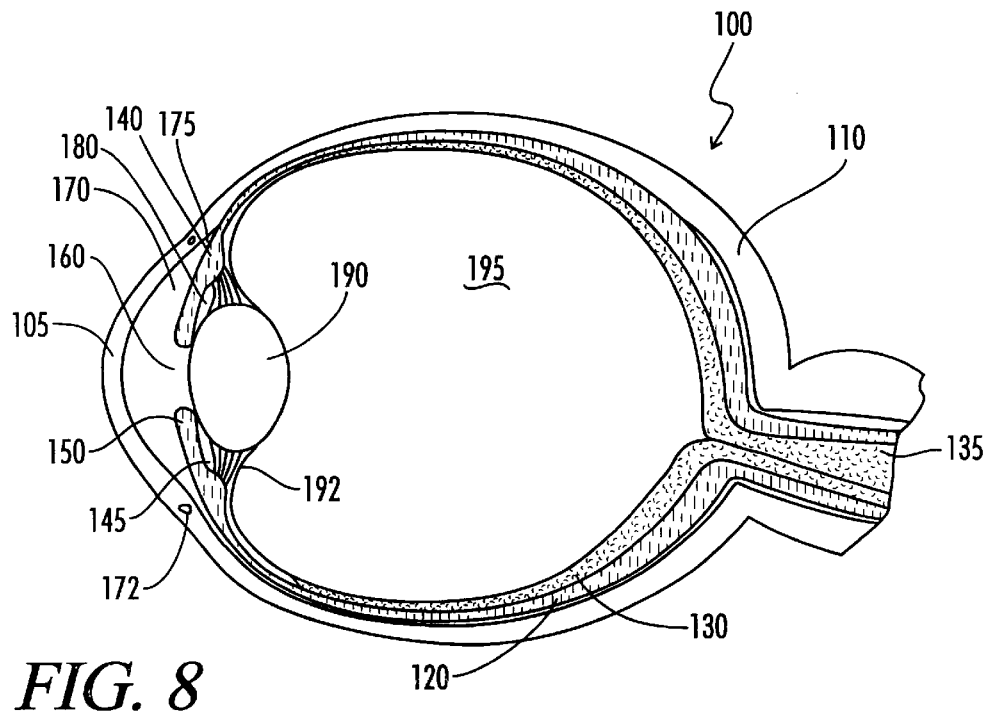
FIG. 8 is a horizontal section of the human eye.

FIG. 8 is a horizontal section of the bulb of the human eye 100 and depicts many of the features of the eye's anatomy discussed above. The eye 100 is coated by three tunics: an outer layer composed of a thick sheath called the sclera 110 covering the posterior ⅚ of the eye, and a transparent covering called the cornea 105 over the anterior ⅙; a middle layer called the choroid 120 posteriorly, containing the vasculature and musculature of the eye, joining the ciliary body 140 and iris 150 anteriorly; and an inner layer called the retina 130, comprising a nervous membrane. The tunics are pierced posteriorly by the optic nerve 135 and blood vessels of the retina. The iris 150 is an opaque diaphragm having an aperture called the pupil 160 at its center, and expands or contracts the opening of the pupil 160 by contracture and relaxation of the ciliary muscle in the ciliary body 140 to regulate the flow of light into the eye 100. The natural crystalline lens 190 is suspended between the iris 150 anteriorly and the vitreous body 195 posteriorly by ligaments known as the zonules of Zinn 192 attached to the muscles of the eye 100 in the ciliary body 140. At the junction between the iris 150 and the ciliary body 140 is a shallow depression known as the ciliary sulcus 145. The iris 150 and pupil 160 divide the anterior region of the eye 100 into the anterior chamber 170 and the posterior chamber 180, which are filled with the aqueous humor, a fluid secreted by the ciliary process and flowing from the posterior chamber 180 through the pupil 160 into the anterior chamber 170. At the angle 175 of the anterior chamber 170 (at the junction of the cornea 105, and the iris 150), the fluid is filtered through the spaces of Fontana and the pectinate villi and drains through the sinus venosus sclerae, or canals of Schlemm 172. The lens 190 is contained within a thin membrane called the lens capsule (not shown).

The haptics 60 of the present invention may be used for implants into the anterior chamber 170, the posterior chamber 180, or the posterior portion of the lens 190 capsule. FIG. 11 shows the conformation of the IOL, 10 for implantation in the anterior chamber 170 of an aphakic eye. As shown in the plan view, the optic 20 is in an anterior plane, and the stems 30 are angled posteriorly so that the optic 20 is vaulted anteriorly, with the footplates 70 occupying a plane posterior to the tips 50 of the stems 30. FIG. 12 shows the conformation of an IOL 10 of the present invention for implantation in the posterior chamber 180 of an aphakic eye. As shown in the plan view, the optic 20 is in a posterior plane, and the stems 30 are angled posteriorly so that the optic 20 is vaulted posteriorly, with the footplates 70 occupying a plane anterior to the tips 50 of the stems 30. FIG. 13 shows the conformation of the IOL 10 for implantation in the posterior chamber 180 of a phakic eye. As shown in the plan view, the optic 20 is in a posterior plane, and the stems 30 are angled posteriorly so that the optic 20 is vaulted posteriorly, with the footplates 70 occupying a plane anterior to the tips 50 of the stems 30.

It will be appreciated that in each of the three conformations shown above, the optic 20, the tip 50 of the stem 30, and the footplates 70 of the haptics 60 each occupy a different frontal or coronal plane, with the tip 50 of the stem 30 always occupying the middle plane. When the haptics 60 are released, the footplates 70 occupy positions superior, inferior, and lateral to the stems 30. As a consequence of this geometry, in this embodiment the stems 30 do not come into contact with a tissue of the eye 100, and are prevented from lacerating or damaging the tissues.

It will also be appreciated that when the haptics 60 are released in the eye 100, the haptics 60 expand so that, in the average human eye 100, the footplates 70 rest on the circumference of a circle concentric with the optic 20 and subtend four substantially equal arcs of 90° each about the circumference of the circle. The footplates 70 are so sized and shaped that surface contact with and pressure applied to the tissues of the eye 100 are kept to a minimum to avoid complications due to swelling, lacerations or other damage to the eye tissue. For phakic eyes, a corrective IOL may be implanted with the lens 10 centered in the anterior chamber 170, the footplates normally resting in the angle 175 of the anterior chamber 170, or in the posterior chamber 180 between the iris 150 and the natural lens 190, the footplates 70 normally resting in the ciliary sulcus 145. For aphakic eyes, the IOL 10 may be implanted in the anterior chamber 170 with the footplates 70 normally resting in the angle 175 of the anterior chamber 170, or in the posterior chamber 180 with the footplates 70 normally resting in the ciliary sulcus 145, or in the capsular bag with the footplates 70 within and stretching the posterior portion of the capsule of the lens 190.

Figure 9:
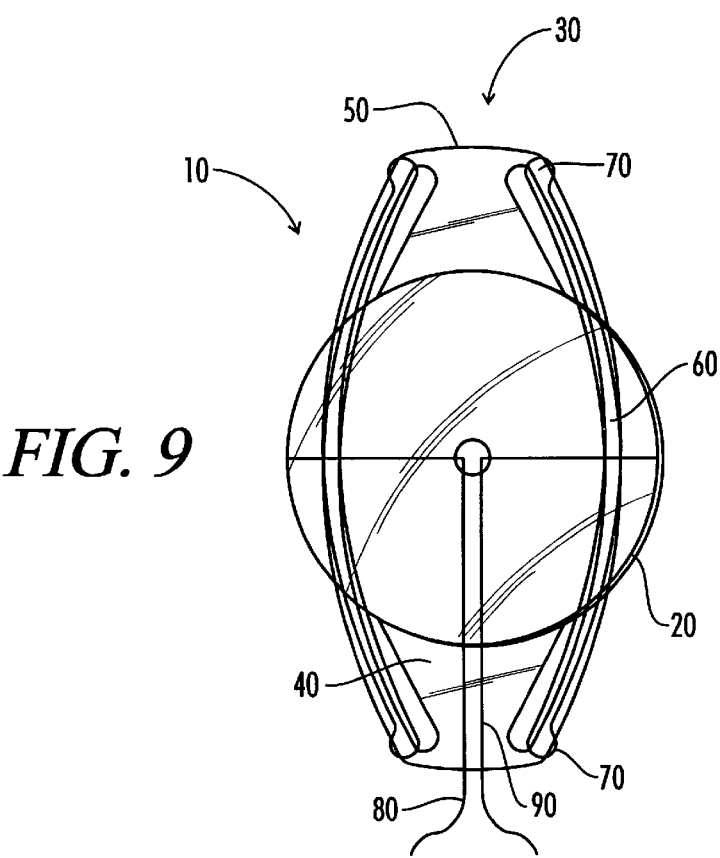
FIG. 9 is a view of crossed haptics for intraocular lenses according to the present invention with the lens and haptics compressed for insertion into the eye.
Figure 10:
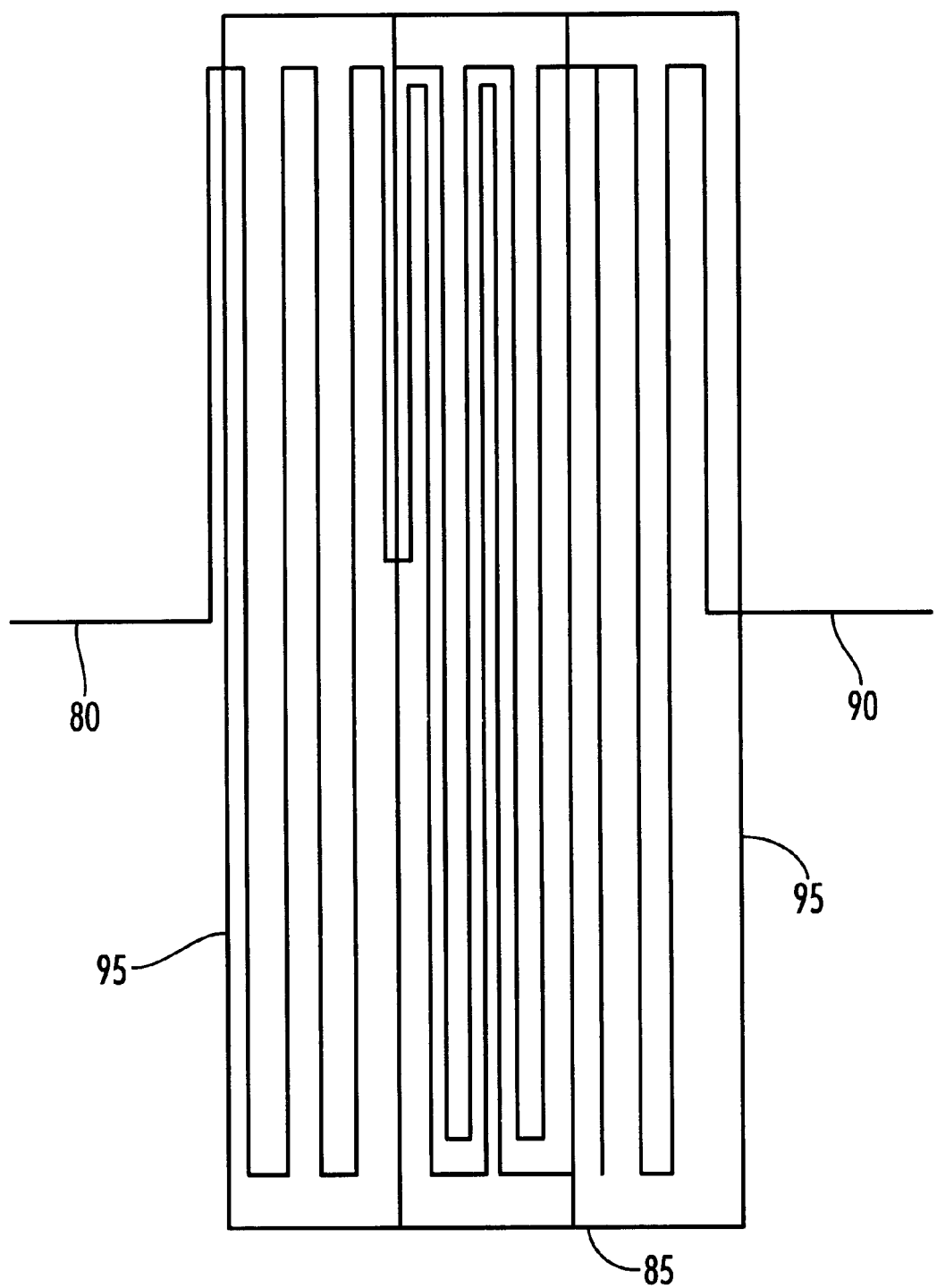
FIG. 10 is a plan view showing the preparation of suture material used to insert the lens of the present invention into the eye.

A method for implanting the haptics 60 and releasing the haptics 60 after implantation in the eye 100 can now be described. A piece of suture material is cut into a first piece 80 and a second piece 90 which are seriated as shown in FIG. 9. The two pieces of suture material are sequenced with a pair of outer zones 95, each with a single thread arranged in substantially S-shaped loops, and a center zone 85 between the two outer zones 95, in which the first piece and the second piece have overlapping lengths with the S-shaped loops paralleling each other. The suture material is coated with a viscoelastic material which is unreactive to and harmless to the eye 100, preferably a heavy layer or paste of chondroitin sulfate, and allowed to dry. The center zone 85 may receive a second coat of the viscoelastic material to ensure that the center zone 85 has a thicker layer of the viscoelastic material than the outer zones 95 and that the first piece 80 is temporarily bonded to the second piece 90.

After the viscoelastic material has dried, the seriated suture material is tied around the lens 10 until the optic 20 is deformed into a tube and the haptics 60 are compressed and tucked either anteriorly or posteriorly to the optic 20, as shown in FIG. 9. The surgeon inserts the lens 10 into a minimal incision in the cornea 105 or sclera 110 and positions the lens 10 in the eye 100, leaving a loose end of first piece 80 and second piece 90 outside the eye. After positioning the lens 10, the surgeon inspirates an irrigating solution, preferably saline solution, onto the viscoelastic paste, which dissolves the paste. Since the outer zones 95 have a thinner layer of paste, the outer zones 95 tend to dissolve before the center zone 85. As the paste dissolves, the S-shaped loops of the outer zones tend to unwind and lengthen, releasing the haptic 60 arms, which spring back to their original conformation due to the memory characteristics of the lens 10 material, the surgeon tweaking the position of the lens 10 by manipulating the haptics as they unwind, if necessary. By the time the outer zones 95 are free of the viscoelastic paste, the outer edges of the footplates 70 rest against the tissue of the eye 100 in a circular pattern. The size of the circle depends on the size of the eye 100. Typically, the human eye 100 is 11.5 to 13.5 mm in diameter.

Additional irrigating solution is inspirated to the center zone 85 until all the paste is dissolved, separating the first piece 80 of suture material from the second piece 90. The suture material can then be removed from the eye 100 by gently pulling the loose end of first piece 80 or second piece 90.

Thus, the crossed haptics 60 of the present invention and the method of inserting and releasing the haptics 60 present a means for supporting an IOL 10 which offers improved centering of the lens 10 while minimizing damage to the tissue of the eye 100.

In another embodiment of the present invention, the lens is rolled and passed through the cornea. This method is discussed below and in U.S. Ser. No. 08/914,767 (filed Aug. 20, 1997 and incorporated herein by reference). This is a preferred method of insertion for the embodiment of the present invention discussed below.

A preferred embodiment of the present invention is depicted in FIG. 14. In this embodiment, to achieve strength, the current haptic design has a transition area, 2. The haptic transition area, 2, starts at the optic edge with a wide area in contact with the edge of the optic. The transition area is the same thickness as the optic edge where the transition area and the optic edge are in contact, 3. As the haptic transition area extends radially away from the optic, the member narrows, 4, until a desired width to allow the maximum shear stress from bending to remain relatively constant. As the distance from the optic increases radically, the thickness of the haptic is increased. The wide area of the haptic at the optic edge adds strength to the structure while allowing flexibility of the optic for rolling. Axial flexibility is less desirable once the transition to the haptic has been achieved, so the thickness of the haptic increases as the width decreases. The cross sectional area has changed in width and thickness in such a ratio as to allow the maximum shear stress from bending to remain relatively constant.

The length of the haptic is also proportional to the amount of force required to flex the haptic through a given distance. One method of increasing the effective length of the haptic on the current invention is splitting the haptic, 5. At the radial distal end of the haptic transition area the haptic is split into two members. The members, 6, travel parallel for some distance, which allows the haptic to move further away from the optic. As the haptic extends radically until approaching tissue when implanted in a small eye the haptic changes direction, 7, and moves toward a point approximately 15–30 degrees, preferably 25 degrees, from the center line, 8, of the haptic transition area and along a radically outward circle, 9, that is the desired maximum size of the haptics. The outer edge, 11, of the haptic footplate, 70, rests tangentially to the radically outward circle, 9, that is the desired maximum size of the haptic. The haptic arms, 60, are bent to where the footplates, 70, are placed inside the optic area, 20. The optic area is rolled to where the footplates are enclosed inside the optic area for ease of insertion into the eye through a small incision.

Since the force necessary to deflect the lens three millimeters is significantly less than the force required to flex the current state of the art lens one millimeter, much less force is exerted on the tissue of the eye. Therefore, the thickness of the footplates, 70, can be significantly thinner than for the current lens designs and the force exerted on the tissue of the eye is still much less per square area than the current state of the art lens. A lens manufactured to the current state of the art will rest just toward the center of the eye from Schlemm's canal, which will effectively block the canal in the area where the footplates are located. A thin lens footplate will rest toward the iris from Schlemm's canal and not block the flow of aqueous out of the eye.

In this embodiment of the present invention, the haptics are placed inside a rolled optic and return to their natural shape after the optic was unrolled. A desirable feature of the crossed haptic embodiment of the present invention is the four haptic footplates, which are all independently attached to the optic transition area. Therefore, if one haptic is positioned against tissue that is smaller in diameter than the tissue where another haptic is resting, the movement of one haptic does not cause the second haptic to have substantially less or more force to hold the lens haptic in position. This fact gives the lens extremely good centration. In this embodiment of the present invention, the haptics may be optionally crossed.

The success of the crossed haptic design is due to the length of the haptics and its small cross sectional area. The flexibility of the haptic is proportional to the third power of the length of the haptic. Therefore, this embodiment lengthens the haptic without moving the haptics more than the width of the incision away from the centerline of the haptic transition area. At the radial distal end of the haptic transition area where the haptics are split into two members, 6, the outside width of the two combined haptics cannot be wider than the desired incision size to implant the lens.

The haptic arms, 6, 60, extend radially outward to a position where the change in direction, 7, occurs before contacting tissue when the lens is placed in the eye. In addition to increasing the haptic arm distance, the haptic arm width and thickness are controlled. The thickness of the haptic arm controls the amount of movement of the lens in the axial direction (i.e., it controls axial anterior displacement). The thicker the haptic arm, the less anterior displacement will occur. Due to the fact that thickness is inversely proportional to the third power of the thickness, when forces acting to bend the haptic along the axial plan is applied, there is much less anterior displacement of the optic.

When considering force applied to bend the haptics in a radial plane the deflection of the lens haptic is inversely proportional to the third power of the width of the haptic. Therefore to obtain the desired dimensions the haptics approach the thickness of the current state of the art lens, but are significantly thinner in width. This allows the lens haptic to have good strength, while being very rigid in the axial direction, yet being extremely flexible in the radial direction. Since the lens design reduces the amount of force required to flex the lens the haptic footplates, 11, can be significantly thinner. For a standard state of the art lens, the footplates are between 200 and 250 microns.

The large footplates block the trabecular meshwork and add significant force to Schlemm's Canal at the contact points of the footplates. This embodiment of the present invention allows the use of a footplate that is about 50 or less microns thick.

The haptic arms, 60, are bent to where the haptic arms and the haptic footplates, 70, are inside the optic area, 20. The optic area is then rolled with the haptics remaining inside. The rolled optic then acts as a guide or conduit to carry the haptics through the wound. As the optic is inserted through the wound the wound holds the optic rolled until the optic starts opening inside the eye. As the optic opens the haptics are freed to move into position within the eye. The optic configuration is covered under patent application Ser. No. 08/914,767, incorporated herein by reference.

Preferred embodiments of the present invention are thin lens optics where the optic when made of PMMA, are approximately 15–35 microns thick, preferably about 22–28, and more preferably about 25 microns thick at the thinnest point and about 75–95 microns thick, preferably about 82–87 microns thick, most preferably about 85 microns thick at the thickest point. The optic diameter is approximately 40–60 microns thick, preferably about 45–55, and most preferably about 50 microns thick. The haptic transition area starts at about the thickness of the optic diameter (most preferably about 50 microns) and increases in thickness about three times (preferably to about 150 microns thick). At the point where the haptic transition thickness reaches the desired thickness, the haptic transition area has reached a width of approximately 400–700 microns, preferably about 450–550, most preferably about 500 microns. After flexing the haptics, the radially distal most part of the curve should be less than the width of the desired incision. For the preferred embodiment the desired incision is about 3 millimeters. To obtain the desired flexibility the width of the haptic is preferably about 100 microns wide. The length of the haptic radially from the center of the optic to where the haptic changes direction is preferably about 5.5 millimeters. The curve at the end of the radial arm of the haptic is about 375 microns in radius and traverses about 52 degrees of arc. The desired width in conjunction with the desired haptic lengths and shapes allows the lens to have approximately 900 milligrams applied force to flex the lens three millimeters (the preferred incision size). After twenty-four-hours of flexure, the lens has less than 200 milligrams of force. The footplates are one millimeter in diameter, which is the same as the current state of the art; however, the thickness of the footplate is 50 microns.

As discussed above, the lens material may also be constructed out of PMMA, but all the lens of the present invention may also be optionally constructed from any other biologically compatible material. Additionally, the lens optics of the present invention may have varying degrees of convexity or concavity to help obtain particular focusing powers.

All patents, copending applications, articles and publications referred to above are herein expressly incorporated by reference.

The invention thus being described, it would be obvious that the same may be modified in ways that would be understood by one of ordinary skill in the art. It is to be understood that the present invention is not limited to the embodiments described above, and includes such variations. As such, all such variations are intended to be within the scope of the following claims.

We claim:

1. An intraocular lens, comprising:
   a lens optic;
   four haptics independently attached to the lens optic, wherein the movement of or pressure applied by eye tissue to a first haptic does not substantially influence a second haptic's contact with eye tissue, wherein said haptics are attached to the lens optic through a transition area, wherein said transitional area having a first thickness of about that of the edge of the lens optic and expanding to a thickness of about three times the first thickness at a distance from the edge of the lens optic.

2. An intraocular lens, comprising:
   a lens optic having a thickness of about 15 microns to about 95 microns, and having an optic diameter of about 6 millimeters or less;
   four haptics independently attached to the lens optic, said haptics comprising a footplate distally located from the point of attachment to the lens optic; and wherein the four haptics are attached to the lens optic in pairs of two, each pair having a line of symmetry separated from the other by approximately 180 degrees, and wherein each pair of haptics is attached to the lens through a transition area shared by each haptic in the pair, wherein the transitional area has substantially the same thickness of the optic edge, and decreases in width and increases in thickness at a distance from the optic edge.

3. An intraocular lens, comprising:
   a lens optic having a thickness of about 15 microns to about 95 microns, and having an optic diameter of about 6 millimeters or less;
   four haptics independently attached to the lens optic, said haptics comprising a footplate distally located from the point of attachment to the lens optic; and wherein the four haptics are attached to the lens optic in pairs of two, each pair having a line of symmetry separated from the other by approximately 180 degrees, and wherein each pair of haptics is attached to the lens through a transition area shared by each haptic in the pair, wherein the transitional area has substantially the same thickness of the optic edge, and decreases in width and increases in thickness at a distance from the optic edge, wherein the transitional area, at a point distal to the optic edge, increases in thickness to three times the thickness of the optic edge.

4. An intraocular lens, comprising:

a lens optic having a thickness of about 15 microns to about 95 microns, and having an optic diameter of about 6 millimeters or less;

four haptics independently attached to the lens optic, said haptics comprising a footplate distally located from the point of attachment to the lens optic; and wherein the four haptics are attached to the lens optic in pairs of two, each pair having a line of symmetry separated from the other by approximately 180 degrees, and wherein each pair of haptics is attached to the lens through a transition area shared by each haptic in the pair, wherein the transitional area has substantially the same thickness of the optic edge, and decreases in width and increases in thickness at a distance from the optic edge, wherein the transitional areas has a thickness of about 50 microns at the edge of the lens optic, and has a thickness of about 150 microns at its thickest point at a distance from the lens optic.

5. An intraocular lens, comprising:

a lens optic having a thickness of about 15 microns to about 95 microns, and having an optic diameter of about 6 millimeters or less;

four haptics independently attached to the lens optic, said haptics comprising a footplate distally located from the point of attachment to the lens optic; and wherein the four haptics are attached to the lens optic in pairs of two, each pair having a line of symmetry separated from the other by approximately 180 degrees, and wherein each pair of haptics is attached to the lens through a transition area shared by each haptic in the pair, wherein the transitional area has substantially the same thickness of the optic edge, and decreases in width and increases in thickness at a distance from the optic edge, wherein the transitional area has a width of about 500 microns or less at the point distal to the lens optic where the transitional area has reached its thickest point.

6. An intraocular lens, comprising:

a lens optic having a thickness of about 15 microns to about 95 microns, and having an optic diameter of about 6 millimeters or less;

four haptics independently attached to the lens optic, said haptics comprising a footplate distally located from the point of attachment to the lens optic; and wherein the four haptics are attached to the lens optic in pairs of two, each pair having a line of symmetry separated from the other by approximately 180 degrees, and wherein each pair of haptics is attached to the lens through a transition area shared by each haptic in the pair, wherein each pair of haptics extends from the optic parallel one haptic to the other for a distance before extending symmetrically around the circumference of the optic in opposite directions to a point about 15–30 degrees from a center line in the optic that is perpendicular to the point where the haptics are attached to the optic.

7. An intraocular lens, comprising:

a lens optic having a thickness of about 15 microns to about 95 microns, and having an optic diameter of about 6 millimeters or less;

four haptics independently attached to the lens optic, said haptics comprising a footplate distally located from the point of attachment to the lens optic; and wherein the four haptics are attached to the lens optic in pairs of two, each pair having a line of symmetry separated from the other by approximately 180 degrees, and wherein each pair of haptics is attached to the lens through a transition area shared by each haptic in the pair, wherein each pair of haptics extends from the optic parallel one haptic to the other for a distance before extending symmetrically around the circumference of the optic in opposite directions to a point about 15–30 degrees from a center line in the optic that is perpendicular to the point where the haptics are attached to the optic, wherein the length of the first and second haptic in a pair extend from the center of the optic to the point where the first haptic turns opposite the second haptic is about 5.5 millimeters to form a radial arm.

8. The intraocular lens of claim 7, wherein the radial arm has a curve at the end of the radial arm of the haptic, wherein said curve is about 375 microns in radius and traverses about 52 degrees of arc.

9. An intraocular lens, comprising:

a lens optic;

two pairs of haptics attached to the lens optic, each pair being located at a diametrically point about 180 degrees from the other;

a footplate at a point on each haptic distally located from the lens optic;

wherein said lens optic is from 15–95 microns thick, with the lens optic diameter being from about 5 millimeters to about 6 millimeters;

wherein each pair of haptics is attached to the lens optic through a transitional area that starts at a thickness of that of the lens optic diameter, and expands to three times the thickness of the lens optic diameter at a distance from the lens optic diameter; and wherein the haptics in each pair extend from the lens optic in a parallel manner one haptic to the other for a distance of about 5.5 millimeters from a center of the lens optic before turning opposite directions around the edge of the lens.

10. The intraocular lens of claim 9, wherein the diameter of the lens optic is about 6 millimeters.

11. The intraocular lens of claim 9, wherein the haptic width substantially along its length is about 100 microns.

12. The intraocular lens of claim 9, wherein said haptics exert less than 300 milligrams of force after 24 hours of haptic flexure.

13. The intraocular lens of claim 9, wherein said footplate is 1 millimeter in diameter and 50 microns thick.

14. The intraocular lens of claim 9, wherein said haptics, after turning an opposite direction from the corresponding haptic in its pair, move to a point approximately 15–30 degrees from a center line in the lens optic.

15. The intraocular lens of claim 9, wherein said haptics, after turning an opposite direction from the corresponding haptic in its pair, move to a point approximately 25 degrees from a center line in the lens optic.

* * * * *